(12) United States Patent
Glaser-Seidnitzer et al.

(10) Patent No.: US 8,719,689 B2
(45) Date of Patent: May 6, 2014

(54) METHOD AND USER INTERFACE FOR IMPLEMENTATION OF A MEDICAL EXAMINATION

(75) Inventors: Karlheinz Glaser-Seidnitzer, Fuerth (DE); Johannes Kling, Zurich (CH); Martin Requardt, Nuremberg (DE)

(73) Assignee: Siemens Aktiengesellschaft (DE)

( * ) Notice: Subject to any disclaimer, the term of this patent is extended or adjusted under 35 U.S.C. 154(b) by 385 days.

(21) Appl. No.: 12/420,209

(22) Filed: Apr. 8, 2009

(65) Prior Publication Data

US 2009/0254201 A1   Oct. 8, 2009

(30) Foreign Application Priority Data

Apr. 8, 2008 (DE) .......................... 10 2008 017 829

(51) Int. Cl.
*G06F 17/00* (2006.01)

(52) U.S. Cl.
USPC ........................... 715/217; 715/212; 715/220

(58) Field of Classification Search
CPC .................................................. G06F 17/246
USPC .................. 715/212, 220, 771, 833, 776, 217
See application file for complete search history.

(56) References Cited

U.S. PATENT DOCUMENTS

| 5,621,876 | A  | * | 4/1997  | Odam et al. ................... | 715/212 |
| 5,632,009 | A  | * | 5/1997  | Rao et al. ...................... | 715/201 |
| 5,883,635 | A  | * | 3/1999  | Rao et al. ...................... | 345/440 |
| 6,185,582 | B1 | * | 2/2001  | Zellweger et al. ............ | 715/212 |
| 6,256,649 | B1 | * | 7/2001  | Mackinlay et al. ........... | 715/212 |
| 6,952,808 | B1 | * | 10/2005 | Jamieson et al. ............. | 715/833 |
| 6,993,114 | B2 | * | 1/2006  | Takasawa ..................... | 378/98.5 |
| 2005/0033455 | A1 | * | 2/2005 | Kasdan et al. ................. | 700/12 |
| 2007/0016442 | A1 | * | 1/2007 | Stroup ............................ | 705/2 |
| 2007/0130515 | A1 | * | 6/2007 | Maas ............................ | 715/526 |
| 2007/0162159 | A1 | * | 7/2007 | Ladenburger .................. | 700/17 |

OTHER PUBLICATIONS

Leung et al., A Review of Taxonomy of distortion-Oriented Presentation TEchniques, Jun. 1994, ACM Transaction of Computer-Human Interaction, vol. 1, No. 2., pp. 126-160.*
Patrick Blattner, Using Microsoft Excel 2003, Sep. 2003, Que, p. 370-372.*
Leung et al., A Review of Taxonomy of distortion-Oriented Presentation Techniques, Jun. 1994, ACM Transaction of Computer-Human Interaction, vol. 1, No. 2, pp. 126-160.*
"A Framework for Designing Fisheye Views to Support Multiple Semantic Contexts," Janecek et al., Proc. Working Cof. on Advanced Visual Interfaces (2002) pp. 51-58.

* cited by examiner

*Primary Examiner* — Cesar Paula
*Assistant Examiner* — Howard Cortes
(74) *Attorney, Agent, or Firm* — Schiff Hardin LLP

(57) ABSTRACT

In a method for the implementation of a medical examination via the user interface of at least one imaging device, parameter values in a group of measurement parameters are determined, and are entered via an input device of the user interface. Spatially resolved image information are generated by the at least one imaging device depending on the group of measurement parameters, and the image information is stored on a storage medium. The image information are presented as a data symbol on a screen of the user interface. In order to present the parameters and dependencies to enable a more efficient work process, each measurement parameter of the group of measurement parameters is respectively presented on the screen in a measurement parameter cell of a matrix with multiple rows and multiple columns. The measurement parameters can be contained at least in part in multiple measurement parameter cells. The presentation size of the multiple columns of the matrix depends on their distance from the pointer symbol on the screen.

5 Claims, 3 Drawing Sheets

| xczuj | ghjg | ecbt | vrzz | sdhr |
|---|---|---|---|---|
| vcnm | ghjk | zmul | cwegf | egsd |
| tzum | bmmj | edbt | sfver | xbtuz |
| dfcv | sfsd 9— | ymjd = 3.00mm | ntrth | vvgb |
| anje | cdfhj | qxws | vrzj | wged |
| 7—ymjd: 3.00 mm ⇕ | mjzh | rbun | wwsrg | xdfh |
| ymdl —5 | vbbc | nnjth | xfhr | cghe |
| werm | jtjd | gvntg | dgnt | ymjd = 3.00mm —9 |
| yhjwe | fujk | tnuj | dhtj | eetr |

FIG 2

| xczuj | ghjg | ecbt | vrzz | sdhr |
| vcnm | ghjk | zmul | cwegf | egsd |
| tzum | bmmj | edbt | sfver | xbtuz |
| dfcv | sfsd | ymjd | ntrth | vvgb |
| anje | cdfhj | qxws | vrzj | wged |
| ymjd | mjzh | rbun | wwsrg | xdfh |
| ymdl | vbbc | nnjth | xfhr | cghe |
| werm | jtjd | gvntg | dgnt | ymjd |
| yhjwe | fujk | tnuj | dhtj | eetr |

FIG 3

| xczuj | ghjg | ecbt | vrzz | sdhr |
| vcnm | ghjk | zmul | cwegf | egsd |
| tzum | bmmj | edbt | sfver | xbtuz |
| dfcv | sfsd | ymjd | ntrth | vvgb |
| anje | cdfhj | qxws | vrzj | wged |
| ymjd | mjzh | rbun | wwsrg | xdfh |
| ymdl | vbbc | nnjth | xfhr | cghe |
| werm | jtjd | gvntg | dgnt | ymjd |
| yhjwe | fujk | tnuj | dhtj | eetr |

FIG 4

| xczuj | ghjg | ecbt | vrzz | sdhr |
|---|---|---|---|---|
| vcnm | ghjk | zmul | cwegf | egsd |
| tzum | bmmj | edbt | sfver | xbtuz |
| dfcv | sfsd | ymjd | ntrth | vvgb |
| anje | cdfhj | qxws | vrzj | wged |
| 7~ymjd: 3.00 mm  8 | mjzh | rbun | wwsrg | xdfh |
| ymdl ~5 | vbbc | nnjth | xfhr | cghe |
| werm | jtjd | gvntg | dgnt | ymjd |
| yhjwe | fujk | tnuj | dhtj | eetr |

FIG 5

| xczuj | ghjg | ecbt | vrzz | sdhr |
|---|---|---|---|---|
| vcnm | ghjk | zmul | cwegf | egsd |
| tzum | bmmj | edbt | sfver | xbtuz |
| dfcv | sfsd  9~ymjd=3.00mm | | ntrth | vvgb |
| anje | cdfhj | qxws | vrzj | wged |
| 7~ymjd: 3.00 mm | mjzh | rbun | wwsrg | xdfh |
| ymdl ~5 | vbbc | nnjth | xfhr | cghe |
| werm | jtjd | gvntg | dgnt | ymjd=3.00mm ~9 |
| yhjwe | fujk | tnuj | dhtj | eetr | ic
METHOD AND USER INTERFACE FOR IMPLEMENTATION OF A MEDICAL EXAMINATION

BACKGROUND OF THE INVENTION

1. Field of the Invention

The present invention concerns the setting of measurement parameters for the implementation of medical examinations with imaging methods. In particular, the invention concerns a method and a user interface for implementation of a medical examination.

2. Description of the Prior Art

In software for the implementation of imaging methods in medical technology (for example magnetic resonance tomography, computed tomography, etc.) it regularly occurs that the operator must adapt individual parameters of one or more scan protocols in the data acquisition (known as the "scan"). An access to all possible parameters is sometimes necessary. This turns out to be extremely involved and complicated since, depending on the imaging method, there can be up to 200 parameters. Moreover, very complex and detailed dependencies exist among the individual parameters.

In parameter groups of the type known as the "exam card" of the syngo program that is commercially available from Siemens Healthcare, parameters are distributed among "parameter cards" and "sub-cards" for every individual sequence protocol. These "parameter cards" and "sub-cards" are designated as "Geometry", "Contrast", "Physio" and so forth. Because some parameters should be quickly accessible in multiple situations, they appear simultaneously on two or more cards so that redundancies inevitably occur.

For some measurements with an imaging method (sequence), up to 200 parameters are adjustable that, for example, pertain to the slice count, slice thickness and flip angle as measurement parameters. Many parameter changes thereby affect other parameters; this is handled by a routine known as a Conflict Solver. This is a collection of programmed rules that run in the background and are automatically applied given adjustment of specific constellations of parameter values. A dialog box appears in the user interface in such a case. This informs the operator about the effect of the change on other parameters and presents him or her with the selection to confirm or cancel the change.

These many setting possibilities are complicated and, among other things, confuse the operator.

SUMMARY OF THE INVENTION

An object of the present invention to provide a method and a user interface in order to present the parameters and dependencies so that a more efficient working process is enabled.

The invention is based on setting a presentation (designated as a "fisheye") in order to present the parameters of sequence protocols in the scan. The setting windows are presented in a matrix in which the window size depends on the position of a pointer symbol on the screen. The parameters are simultaneously linked with one another insofar as they are found again in different cells.

The method according to the invention for the implementation of a medical examination via a user interface of at least one imaging device includes the following steps. Parameter values in a group of measurement parameters are determined and entered via an input device of the user interface. Spatially resolved image information are generated by a processor of the at least one imaging device depending on the group of measurement parameters and the image information is stored on a storage medium. The image information is presented (displayed) as a data symbol on a screen of the user interface. Each measurement parameter of the group of measurement parameters is respectively presented on the screen in a measurement parameter cell of a matrix with multiple rows and multiple columns. The measurement parameters can be contained at least in part in multiple measurement parameter cells.

Preferred embodiments of the invention can have one or more of the following additional features:

the position of a pointer symbol on the screen can be controlled via an electromechanical transducer device for the selection of one of the multiple measurement parameter cells, with the presentation size of the multiple columns of the matrix depending on their distance from the pointer symbol on the screen;

the presentation size of the multiple measurement parameter cells in a column of the matrix can depend on their distance from the pointer symbol on the screen, a button symbol to alter the parameter values of the measurement parameter can be displayed in that measurement parameter cell that has the least distance from the pointer symbol on the screen.

a button symbol to alter the parameter values of the measurement parameter can be displayed in that measurement parameter cell whose distance from the pointer symbol on the screen lies below a predetermined threshold;

given a change of a parameter value in a measurement parameter cell, all measurement parameter cells in which this parameter value is adjustable can be shown larger.

The method according to the invention is realized with a user interface of at least one imaging device for the implementation of a medical examination with: an input device for the input of parameter values in a group of measurement parameters, a storage medium to store spatially resolved image information that was generated with the at least one imaging device depending on the group of measurement parameters; a screen for the presentation of the image information as a data symbol, with the group of measurement parameters being presented simultaneously in a matrix with multiple rows and multiple columns on the screen, the measurement parameters being contained at least partially in multiple measurement parameter cells.

The user interface is advantageously provided with an electromechanical transducer device to affect the position of a pointer symbol on the screen for the selection of one or more measurement parameter cells, with the presentation size of the multiple columns and/or rows and/or measurement parameter cells of the matrix depends on their distance from the pointer symbol on the screen.

It is an advantage of the invention that the workflows in the image acquisition can be optimized to a significant degree for the following reasons. The parameters are more easily found because they are identifiable not only via the column names but additionally via the (relative) position in the two-dimensional area. The cognitive effort is reduced because the user interface is more clear (input fields are only displayed upon focusing) and demand less memory capacity of the operator. The navigation is simpler (sub-cards are omitted, redundancies are remedied, the user interaction is inherently faster and requires less effort). Automatic parameter adaptations (Conflict Solver) no longer interrupt the workflow; its results are clearly shown; alterations can be made quickly, be clearly visualized and be canceled.

BRIEF DESCRIPTION OF THE DRAWINGS

FIGS. 2 through 5 respectively show the matrix according to FIG. 1 with a pointer symbol after various durations of residence of the pointer symbol on a parameter cell.

DESCRIPTION OF THE PREFERRED EMBODIMENTS

Figure 1:
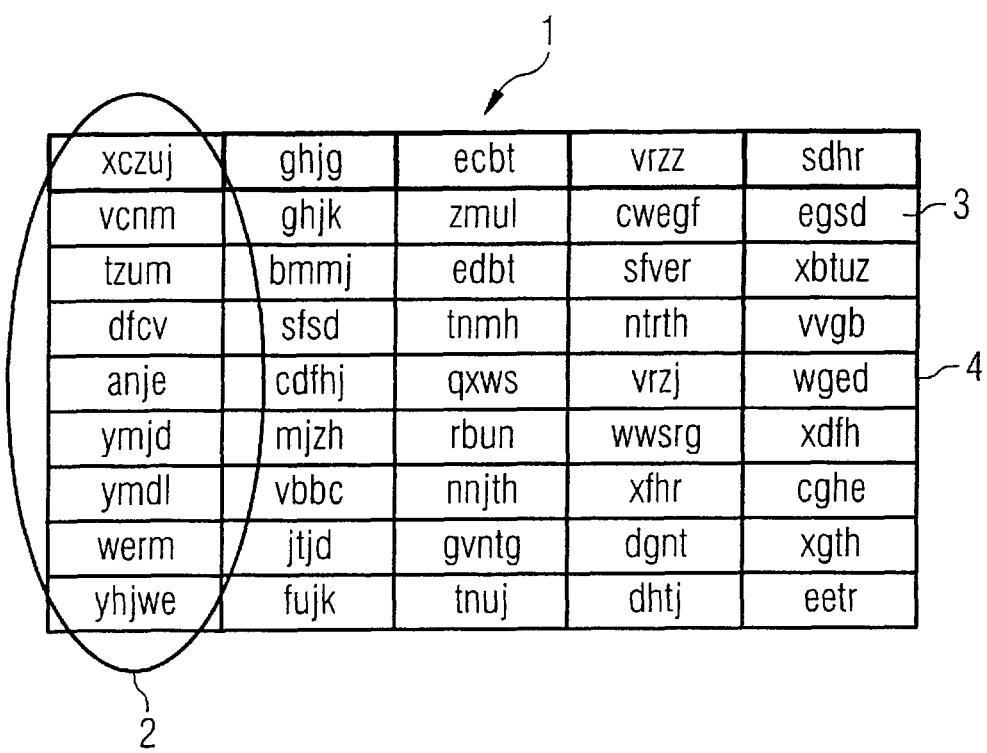
FIG. 1 shows an embodiment of the parameter matrix according to the invention, with rows and columns.

A matrix 1 as it is displayed on a screen of a user interface is shown in FIG. 1. Those measurement parameters that belong to a common theme are collected in columns 2 in the matrix 1. For example, these can be parameters that specify a "routine" in the image acquisition (for example with a magnetic resonance apparatus) for a medical examination. These parameters are "Slice group", "Slices", "Distance" etc. A different group of measurement parameters can be collected under the heading "Geometry", and this group contains the parameters "Multislice mode", "Series", "Links", for example. Additional groups are "Contrast", "System" and "Physio". The group designations are shown in bold face as column headings in this embodiment.

In the shown embodiment, initially only designations 3 of the measurement parameters in individual measurement parameter cells 4 are indicated in the matrix itself, thus the cited terms "Slice group", "Slices", "Distance". Instead of concrete terms, here abstract letter sequences "xczuj", "ghjg", "ecbt" etc. are shown in the representation. The actual parameter values of the measurement parameters 3 are not presented in the cells 4.

Overlaps of the individual measurement parameters 3 can occur in the measurement parameter groups 2. For example, it is thus possible that a measurement parameter occurs both in the one group and in another group for reasons of quick access. In the example shown in Figures, the parameter "ymjd" is cited in the fifth cell of the first column, and in the third column in the third cell, and in the fifth column in the seventh cell.

The matrix 1 shown in FIG. 2 is the same as in FIG. 1 in terms of content, but with multiple columns 2 in which the respective measurement parameters 4 are listed in the individual measurement parameter cells 4. Another pointer symbol 5 is additionally shown in FIG. 2 that a user can move across the screen by means of an electromechanical transducer device (mouse, trackball, touchpad among others) in order to therewith activate specific elements on the screen and select and subsequently-modify them. In the situation shown in FIG. 2, the pointer 5 has been moved by the user to the first column 2 of the matrix 1. If the pointer is held or moved for a specific (short) duration in this situation, the corresponding column 2 is recognized as a region that the user has a closer interest in. In order to simplify the editing of the objects of interest on the screen for the user, the respective column is thereupon shown enlarged. This can occur at the cost of adjacent columns 2 (i.e. if the space on the screen is limited), among other things. In the case shown in FIG. 2, the remaining columns (i.e. those next to the column of interest) are shrunk in terms of their width to the same degree as that with which the column of particular interest is enlarged. Overall, the space requirement demanded on the screen by the matrix 1 therefore remains unchanged.

The pointer 5 does not necessarily need to remain motionless in the column. It is just as possible that the pointer 5 is continuously moved in the column. The single condition for the change of the presentation of the matrix is that the System recognized that a presentation parameter (here: the horizontal coordinate) no longer changes. The other presentation parameters aside from that selected (other horizontal coordinates aside from "left column") are then classified as unimportant to the user and therefore optically recede behind the parameters important to the user.

As is clear from FIG. 3, this technique is not limited to the selection of columns but rather can be applied just as well to the rows of a matrix. In FIG. 3, a row 6 of the matrix 1 on which the pointer 5 resides for a longer period is shown with its height enlarged. Here it also naturally applies that the pointer does not need to be held or, respectively, fixed unmoving on one spot on the screen; it can easily be moved back and forth in the horizontal direction; the system must only recognize that the other vertical coordinates are clearly not of interest to the user. For this it is necessary to keep the pointer in a narrow range in the horizontal direction for a predetermined time.

Moreover, it is possible (as indicated in FIG. 3) to simultaneously show Column 2 and Row 6 (in which the pointer 5 is presently located) enlarged. In this case, the row receives a greater cell height and the column receives a greater column width. In the cells of the appertaining Column 2 and in the cells of the appertaining Row 6, the font type of the measurement parameter designation is correspondingly adapted in terms of its size; for example, the size of the font in the reduced fields is 9 pt, the font in the emphasized fields is 12 pt.

If the pointer resides an even longer time in one cell 4 of the matrix 1 without exceeding the cell boundaries, the system detects that only this one cell is of interest and not other cells as well in the same Row 6 or the same Column 2.

As shown in FIG. 4, the system also displays (in addition to the designation for the measurement parameter and its numerical value 7) a button symbol 8 as of the point in time at which it is clear that the user is interested only in a specific cell 4. In the presentation in FIG. 4, this is the measurement parameter in the fifth cell of the first column "ymjd: 3.00 mm". The user is now in the position to also alter the numerical value 7 of the measurement parameter as desired with the button symbol 8. Instead of using the button symbol 8 overlaid in measurement parameter cell 4 in order to alter the parameter value step-by-step, the user can also specifically mark one of the numbers and overwrite it. Naturally, a button symbol is understood as not only the shown double arrow upward and downward, but also all other input possibilities are encompassed, for example a scale or a diagram that respectively contain a "slider" for the graphical manipulation of numerical values, or a drop-down menu, wherein these input possibilities can all be overlaid as small graphics next to the respective parameter. Additional possibilities for the graphical or numerical input are familiar to those skilled in the art and need not be discussed further here.

Simultaneously with the enlarged presentation of the cell of the selected parameter, or somewhat later, all additional measurement parameter cells in which the parameter is likewise contained are displayed just like the actual selected cell. This is indicated with the cells 9 in FIG. 5. In these cells 9, the same entry "ymjd: 3.00 mm" is shown as in the fifth cell of the first column, namely in the third cell of the third column and in the seventh cell of the fifth column. The user is therefore warned or informed that, upon changing the numerical value in the currently selected cell, the value in other cells in other columns and rows is simultaneously affected. The user thus receives a superb overview of the consequences of a change in the presently selected cell for other measurement parameter groups (columns in the matrix).

Not only are those cells that possess an identical entry thereby emphasized, but advantageously also those cells in which the parameter values are automatically modified by the system given a change of the selected cell (in other words, the cells that are indirectly dependent on the currently selected cell).

It is understood that the process of the identification of a cell as being of interest by the system can be shortened because the user directly "clicks" on a cell immediately upon positioning the pointer in that cell.

The identification of a cell as interesting (fisheye view concept) has the following basis: based on the focused region of an arbitrary input device (mouse, keyboard, eye tracking, 3D input device or other) that is indicated by a display element (mouse pointer or other), a program associates a maximum degree of interest with the data object nearest to the current focus. This degree of interest is translated in the representation in that the object is enlarged. The horizontally (and, if present, vertically and diagonally or a third dimension) adjacent data objects likewise receive an increased degree of interest as a value that, however, is less proportional to the distance of the focused data object. The enlargement factor is oriented on the space available in the list/grid/coordinate system.

The user interface therefore is composed of three regions. The first region is a fisheye view matrix in which one of the parameter cards according to the prior art is converted analogously or with similar sorting into columns: ever single parameter possesses its own cell in this matrix. The second region accommodates three segments in which image series are presented; here parameter adjustments can be conducted directly in relation to the already-shown anatomy, for example the positioning of slices. In the third region, given parameter changes a timeline is visible with which the history of the changes can be shown step-by-step and can be cancelled ("Undo/Redo").

The matrix functions via two nested fisheye view lists. The columns react to the horizontal position of the mouse pointer; the rows with the parameters are focused depending on the position. The columns are minimized by default; they react to focusing (thus the movement of the mouse pointer over a column) with enlargement.

If the user has focused on a specific column, a row of this column is focused depending on the vertical mouse position. While unfocused rows only indicate the designation of the parameter and its current value, the input fields are also displayed for their focused rows and their direct neighbors.

Parameter changes that have effects on parameters in other columns are implicitly assumed. As soon as parameters in other columns are altered due to the current change, these parameters are marked in color; moreover, the changes of the value are overlaid in a non-transient manner or for a few seconds.

As soon as the parameter changes have been made, a bar with color markings is overlaid that represents the change history. If the mouse pointer travels over one of the segments, in the matrix it is indicated which parameters would be affected by an "Undo" and how the values would be changed; the same display is also possible for "Redo" actions.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for implementing a medical examination via a user interface of a medical imaging device, comprising the steps of:
   determining parameter values for a group of measurement parameters and entering said parameter values of said group of measurement parameters into a medical imaging device via an input device of a user interface of the medical imaging device;
   in said medical imaging device, generating spatially resolved image information dependent on said group of measurement parameters, and storing said spatially resolved image information on a storage medium;
   accessing said spatially resolved image information from said storage medium and presenting said spatially resolved image information as respective data symbols on a screen of the user interface, each of said data symbols representing one measurement parameter in said group of measurement parameters, but not being said parameter values, with each measurement parameter of the group of measurement parameters being individually represented on the screen by a respective data symbol located by itself in a measurement parameter cell of a matrix with multiple rows and multiple columns, with at least some of said measurement parameters being contained in multiple measurement parameter cells;
   altering a position of a pointer symbol on said matrix on the screen to select one of said multiple measurement parameter cells, as a selected cell, and in said selected cell, then presenting both the data symbol and the value of the measurement parameter represented by that data symbol, and enlarging a presentation size of the selected cell and the presentation size of at least one column among said multiple columns, and the presentation size of at least one of said multiple rows of the matrix on said screen that contains the selected cell, by an enlargement factor that is dependent on the distance of said at least one of said multiple columns from said pointer symbol on said screen;
   also enlarging multiple other measurement cells that contain the same data symbol as said selected cell, in respective columns of said matrix by said enlargement factor that is dependent on a distance of said multiple other measurement cells from the pointer symbol on the screen and also presenting, in said other measurement cells, said data symbol and the volume of the measurement parameter represented by said data symbol; and
   allowing user interaction with said user interface to change the parameter value of the measurement parameter represented by the data symbol in the selected cell and, upon changing said measurement parameter, automatically showing all measurement parameter cells in which the changed measurement is adjustable in a larger presentation size on said screen.

2. A method as claimed in claim 1 comprising also enlarging multiple other measurement cells respective columns and rows of said matrix by said enlargement factor that is dependent on a distance of said multiple other measurement cells from the pointer symbol on the screen.

3. A method as claimed in claim 2 comprising displaying a button symbol on said screen to alter a parameter value of one of said measurement parameters displayed in said measurement parameter cell that has a least distance from said pointer symbol on said screen.

4. A method as claimed in claim 2 comprising presenting a button symbol on said screen that, when activated, alters a parameter value of one of said measurement parameters that has a distance from the pointer symbol on the screen that is below a predetermined threshold.

5. A user interface for implementing a medical examination with a medical imaging device, comprising:
- a processor;
- an input unit allowing determination of parameter values for a group of measurement parameters and entry of said parameter values of said group of measurement parameters into said processor;
- said processor being configured to generate spatially resolved image information dependent on said group of measurement parameters;
- a storage medium at which said spatially resolved image information is stored;
- a display having a display screen;
- said processor being configured to access said spatially resolved image information from said storage medium and to present said spatially resolved image information as respective data symbols on said display screen, each of said data symbols representing one measurement parameter in said group of measurement parameters, but not being said parameter values, with each measurement parameter of the group of measurement parameters being individually represented on the display screen by a respective data symbol by itself in a measurement parameter cell of a matrix with multiple rows and multiple columns, with at least some of said measurement parameters being contained in multiple measurement parameter cells;
- said input unit being configured to alter a position of a pointer symbol on the matrix on the display screen to select one of said multiple measurement parameter cells, as a selected cell, and said processor being configured, in said selected cell, to then present both the data symbol and the value of the measurement parameter represented by that data symbol, and to enlarge a presentation size of the selected cell and the presentation size of at least one column among the multiple columns, of the matrix on said display screen that contain the selected cell, by an enlargement factor that is dependent on the distance of said at least one of said multiple columns from said pointer symbol on said display screen;
- said input unit being configured to also to enlarge multiple other measurement cells that contain the same data symbol as said selected cell, in respective columns of said matrix by said enlargement factor that is dependent on a distance of said multiple other measurement cells from the pointer symbol on the screen and also to present, in said other measurement cells, said data symbol and the volume of the measurement parameter represented by said data symbol; and
- said input unit being configured to allow user interaction with said user interface to change the parameter value of the measurement parameter represented by the data symbol in the selected cell and, upon changing said measurement parameter, to automatically show all measurement parameter cells in which the changed measurement is adjustable in a larger presentation size on said screen.

* * * * *